(12) United States Patent
Ogawa (10) Patent No.: US 9,332,961 B2
(45) Date of Patent: May 10, 2016

(54) ULTRASOUND ENDOSCOPE

(75) Inventor: Tomoaki Ogawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/471,525

(22) Filed: May 15, 2012

(65) Prior Publication Data

US 2012/0226165 A1 Sep. 6, 2012

Related U.S. Application Data

(63) Continuation of application No. PCT/JP2011/075929, filed on Nov. 10, 2011.

(30) Foreign Application Priority Data

Nov. 15, 2010 (JP) .................................. 2010-255277

(51) Int. Cl.
*A61B 8/00* (2006.01)
*A61B 8/12* (2006.01)

(52) U.S. Cl.
CPC .. *A61B 8/445* (2013.01); *A61B 8/12* (2013.01)

(58) Field of Classification Search
CPC .................................. A61B 8/12; A61B 8/445
See application file for complete search history.

(56) References Cited

U.S. PATENT DOCUMENTS

| 5,255,669 A | 10/1993 | Kubota et al. |
| 5,462,522 A | 10/1995 | Sakurai et al. |
| 5,499,630 A | 3/1996 | Hiki et al. |
| 7,815,571 B2 * | 10/2010 | Deckman et al. ............. 600/439 |
| 2003/0045768 A1 | 3/2003 | Hirooka et al. |
| 2004/0049111 A1 | 3/2004 | Hirooka et al. |
| 2007/0232922 A1 * | 10/2007 | Kohno .......................... 600/459 |
| 2008/0119738 A1 * | 5/2008 | Imahashi et al. .............. 600/462 |

FOREIGN PATENT DOCUMENTS

| JP | 07-143985 | 6/1995 |
| JP | 2001-224595 | 8/2001 |
| JP | 2002-306489 | 10/2002 |
| JP | 2003-164455 | 6/2003 |
| JP | 2008-253647 | 10/2008 |

OTHER PUBLICATIONS

European Search dated May 7, 2013 from corresponding European Patent Application No. 11 84 1126.3.

\* cited by examiner

*Primary Examiner* — Amanda Lauritzen Moher
(74) *Attorney, Agent, or Firm* — Scully, Scott, Murphy & Presser, PC

(57) ABSTRACT

An ultrasound endoscope includes: a bending portion; a distal end rigid portion which is located on a distal end side with respect to the bending portion; and a connection portion making up the distal end rigid portion, for connecting the ultrasound observation section with the bending portion, wherein the connection portion is inclined with respect to a central axis of the bending portion, an interface between the connection portion and the bending portion is perpendicular to the central axis, and the connection portion has a swept shape which is obtained by making a cross-section of the interface slide in a direction perpendicular to the central axis while keeping the perpendicularity along a straight line intersecting with the central axis.

5 Claims, 7 Drawing Sheets

ULTRASOUND ENDOSCOPE

CROSS REFERENCE TO RELATED APPLICATION

This application is a continuation application of PCT/JP2011/075929 filed on Nov. 10, 2011 and claims benefit of Japanese Application No. 2010-255277 filed in Japan on Nov. 15, 2010, the entire contents of which are incorporated herein by this reference.

BACKGROUND OF THE INVENTION

1. Field of the Invention

The present invention relates to an ultrasound endoscope including an ultrasound observation section and a connection portion for connecting the ultrasound observation section with a bending portion in a distal end rigid portion, the distal end rigid portion being located on a distal end side with respect to the bending portion in an insertion portion to be inserted into an interior of a body.

2. Description of the Related Art

There is a well-known ultrasound endoscope which repeatedly transmits ultrasound to an area to be inspected in the interior of the body from an ultrasound transmission/reception section, and receives an echo signal of the ultrasound reflected from the area to be inspected with the ultrasound transmission/reception section, thereby enabling observation of an ultrasound image which is a two-dimensional visible image of the area to be inspected.

Japanese Patent Application Laid-Open Publication No. 2002-306489 discloses a structure for improving puncturability, in which a part of a distal end is inclined.

SUMMARY OF THE INVENTION

To achieve the above-described object, an ultrasound endoscope in an aspect of the present invention includes: a bending portion; a distal end rigid portion which is located on a distal end side with respect to the bending portion; an ultrasound observation section making up the distal end rigid portion; and a connection portion making up the distal end rigid portion, for connecting the ultrasound observation section with the bending portion, wherein the connection portion is inclined with respect to a central axis of the bending portion, an interface between the connection portion and the bending portion is perpendicular to the central axis, and the connection portion has a swept shape which is obtained by making a cross-section of the interface slide in a direction perpendicular to the central axis while keeping the perpendicularity along a straight line intersecting with the central axis.

DETAILED DESCRIPTION OF THE PREFERRED EMBODIMENTS

Hereinafter, embodiments of the present invention will be described with reference to the drawings. It is noted that drawings are schematically shown and a relationship between a thickness and a width of each member, a ratio of the thicknesses of respective members, and the like may be different from actual ones, and also it is a matter of course that portions having different dimensional relations and ratios from each other between respective drawings may be included.

First Embodiment

Figure 1:
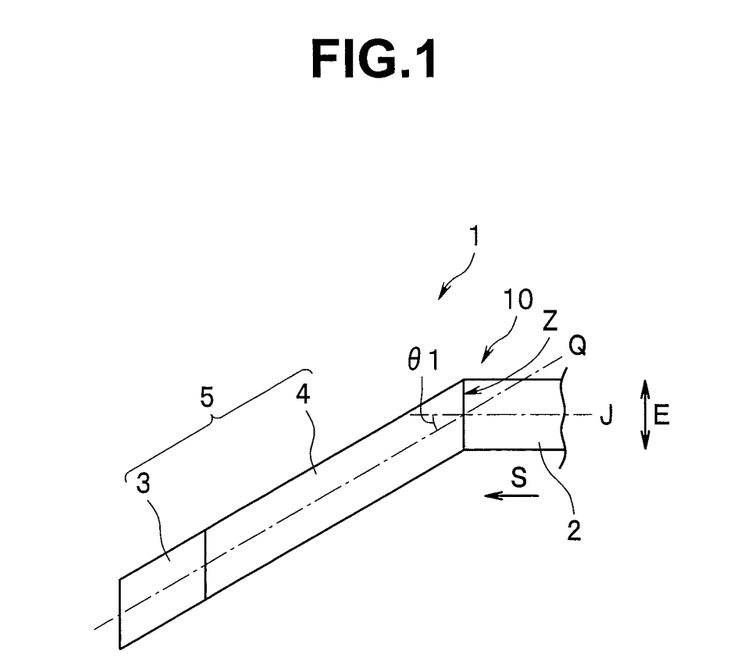
FIG. 1 is a diagram to schematically show the distal end side of an insertion portion of an ultrasound endoscope of a first embodiment.
Figure 2:
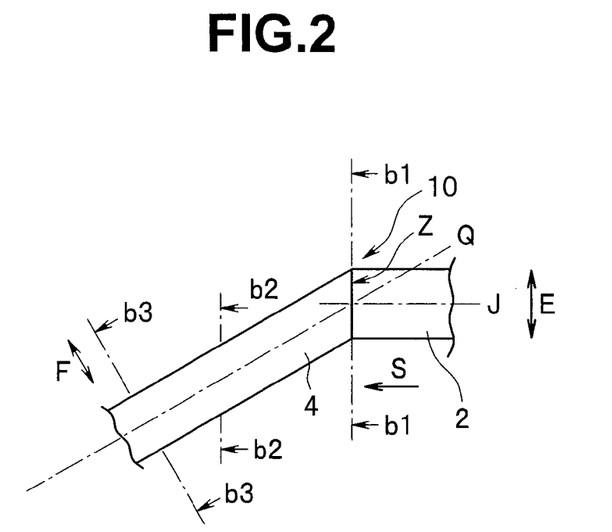
FIG. 2 is a schematic diagram focusing on a part of the insertion portion of FIG. 1.

FIG. 1 is a diagram to schematically show the distal end side of an insertion portion of an ultrasound endoscope of the present embodiment, and FIG. 2 is a schematic diagram focusing on a part of the insertion portion of FIG. 1.

As shown in FIG. 1, an ultrasound endoscope 10 is provided with a known bending portion 2 on the distal end side in a direction S with respect to an insertion portion 1 which is to be inserted into the interior of the body, for example, a bronchus, and is also provided with a non-bending distal end rigid portion 5 on the distal end side in the direction S with respect to the bending portion 2. It is noted that since the configuration of the ultrasound endoscope 10 in the rearward in the direction S with respect to the bending portion 2 is well known, description thereof will be omitted.

A principal part of the distal end rigid portion 5 is configured to include an ultrasound observation section 3 and a connection portion 4. The connection portion 4 connects the ultrasound observation section 3 with the bending portion 2.

It is noted that although not shown in FIG. 1, the distal end rigid portion 5 may be provided with an observation section and an image pickup section for observing the interior of the body, an illumination section for illuminating the interior of the body, and the like. Further, the distal end rigid portion 5 may be provided with a below-described protrusion opening 4g (see FIG. 5) which is opened thereon and from which a treatment instrument passed through the insertion portion 1 is protruded.

Further, the connection portion 4 is inclined by an angle θ1 which is less than 90°, with respect to a central axis J of the bending portion 2 which is parallel with the direction S, as shown in FIG. 1. The angle θ1 herein refers to an angle on the distal end side in the direction S out of the angles formed between the central axis J of the bending portion 2 and the connection portion 4 as shown in FIG. 1.

To be specific, the connection portion 4 is positioned along a straight line Q that intersects with the central axis J at an angle θ1 as shown in FIG. 1. An interface Z between the connection portion 4 and the bending portion 2 is perpendicular to the central axis J, and is configured to have a swept shape which is obtained by making the cross section of the interface Z slide in a direction perpendicular to the central axis J while keeping its perpendicularity along the straight line Q.

To be more specific, as shown in FIG. 2, the connection portion 4 is formed into a shape in which when taking a b2-b2 cross-section in a direction E at whatever position along the straight line Q, the cross-sectional shape corresponds to the shape of a b1-b1 cross-section of the direction E in the interface Z.

In other words, the connection portion 4 is formed into a shape in which the shape of a b3-b3 cross-section of the connection portion 4 in a direction F which is perpendicular to the straight line Q does not correspond to the b1-b1 cross-section in the direction E of the interface Z.

It is noted that in the present embodiment, the ultrasound observation section 3 is also positioned along the straight line Q which intersects with the central axis J at the angle of θ1, as shown in FIG. 1.

Figure 3:
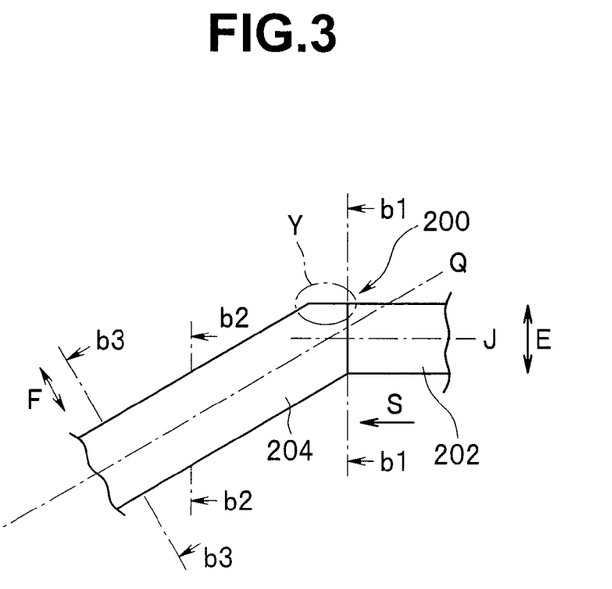
FIG. 3 is a schematic diagram focusing on a part of the insertion portion of FIG. 9.
Figure 9:
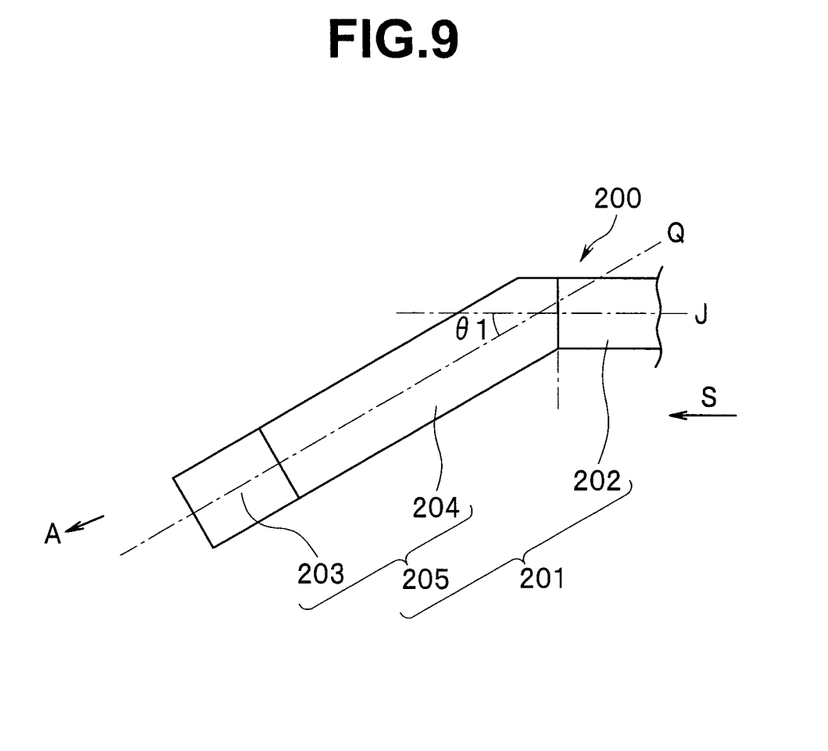
FIG. 9 is a diagram to schematically show an example of an ultrasound endoscope in which a connection portion of an insertion portion does not have a swept shape.

Here, FIG. 9 is a diagram to schematically show an example of an ultrasound endoscope in which a connection portion of an insertion portion does not have a swept shape, and FIG. 3 is a schematic diagram focusing on a part of the insertion portion of FIG. 9.

As shown in FIGS. 3 and 9, in an endoscope 200 in which a connection portion 204 does not have a swept shape, the connection portion 204 is formed into a shape in which the shape of a b1-b1 cross-section of a direction E in the interface Z corresponds to a b3-b3 cross-section of the connection portion 4 in a direction F as shown in FIG. 3, in an insertion portion 201 having a distal end rigid portion 205, which includes an ultrasound observation section 203 and the connection portion 204, and a bending portion 202.

In other words, the connection portion 204 is formed into a shape in which the shape of a b2-b2 cross-section of the connection portion 204 in the direction E does not correspond to the shape of the b1-b1 cross-section of the direction E in the interface Z at whatever position along the straight line Q of the connection portion 204.

That is, the connection portion 4 in the present embodiment is formed into a shape in which a straight area along the direction S surrounded by a chain line Y in FIG. 3, which is present in the connection portion 204 not having a swept shape shown in FIG. 3, is formed into a shape which is not present in a proximal end of the connection portion 4.

It is noted that while the entire connection portion 4 may have a shape obtained by making the interface Z slide along the straight line Q so as to be perpendicular to the central axis J, it may also have a shape in which a part thereof is cut off according to purposes. Moreover, configuration may also be such that a portion which is made to slide so as to be perpendicular to the central axis J and a portion which is made to slide at a certain angle other than perpendicularity with respect to the central axis J may coexist.

In this way, since in the present embodiment, the connection portion 4 has a swept shape, the insertability of the insertion portion 1 is excellent. It is noted that the reason why the insertability of the insertion portion 1 is made excellent by the arrangement that the connection portion 4 has a swept shape will be described later.

Second Embodiment

Figure 4:
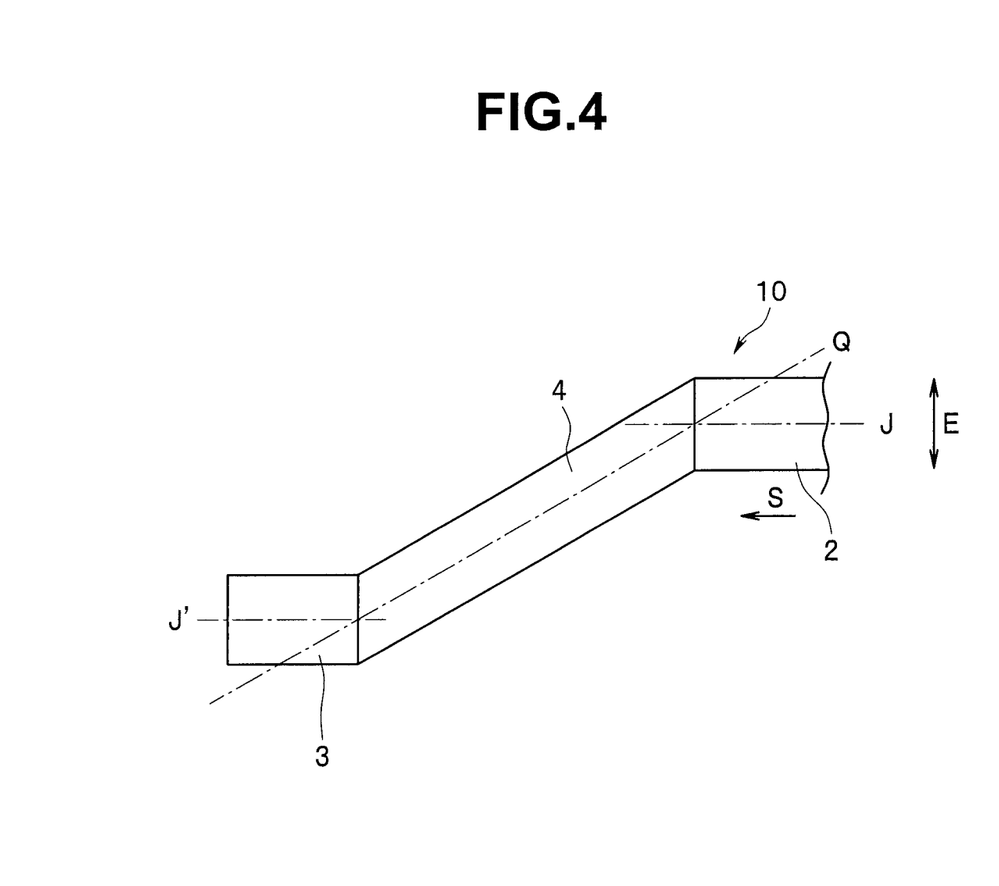
FIG. 4 is a diagram to schematically show the distal end side of an insertion portion of an ultrasound endoscope of a second embodiment.

FIG. 4 schematically shows the distal end side of an insertion portion of an endoscope showing the present embodiment.

As shown in FIG. 4, in the present embodiment as well, the connection portion 4 has a swept shape as in the first embodiment described above.

As a result of this, as in the first embodiment, the present embodiment has a configuration in which the insertability of the insertion portion 1 is excellent. It is noted that the reason why the insertability of the insertion portion 1 is made excellent by the arrangement that the connection portion 4 has a swept shape will be described later.

Further, the present embodiment is configured such that the ultrasound observation section 3 is bent (inclined) from the distal end of the connection portion 4 with respect to the connection portion 4 in the direction of an axis J' which is parallel with the central axis J of the bending portion 2.

As a result of this, the present embodiment has a configuration in which the insertability of the insertion portion 1 is improved than in the first embodiment. It is noted that the reason why the insertability of the insertion portion 1 is improved by the arrangement that the ultrasound observation section 3 is bent will be described later.

Third Embodiment

Figure 5:
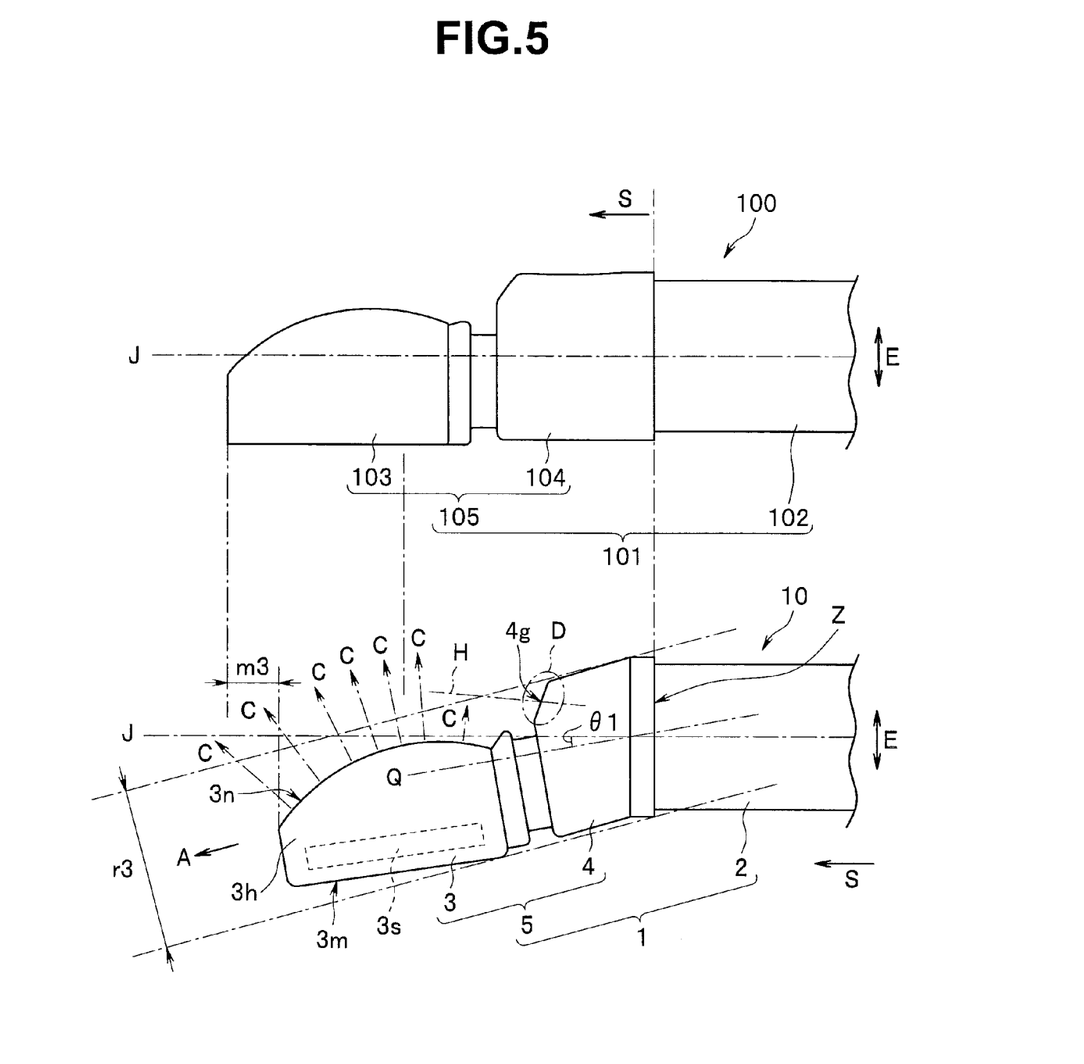
FIG. 5 is a diagram to show the distal end side of the insertion portion of the ultrasound endoscope of the present embodiment, along with the distal end side of a conventional insertion portion shown in FIG. 7 in which a distal end rigid portion along with a bending portion has a linear shape.
Figure 6:
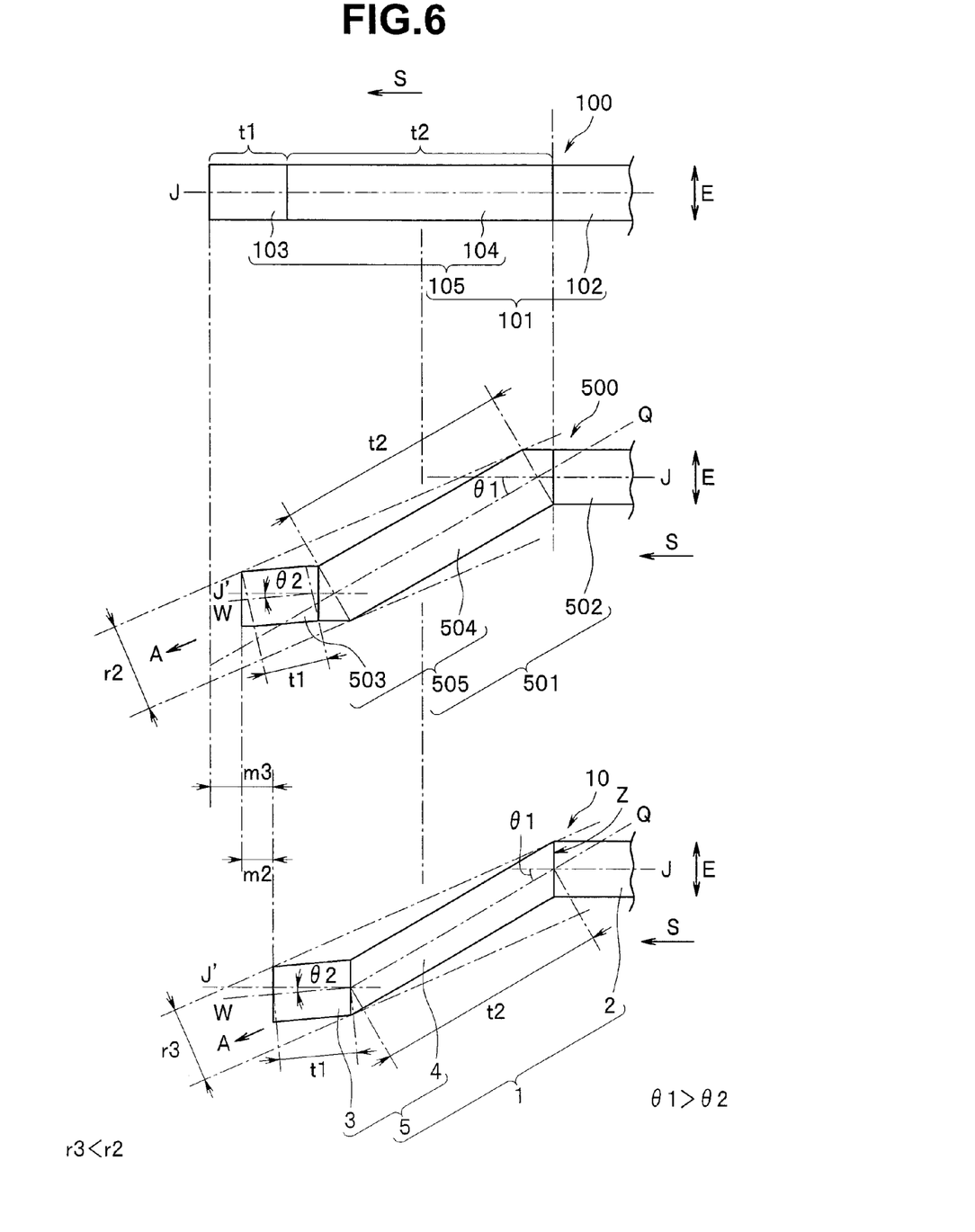
FIG. 6 is a diagram to schematically show the distal end side of the insertion portion of the present embodiment of FIG. 5, along with the distal end side of a conventional insertion portion shown in FIG. 8, and the distal end side of an insertion portion in which a connection portion does not have a swept shape and an ultrasound observation section is bent.
Figure 7:
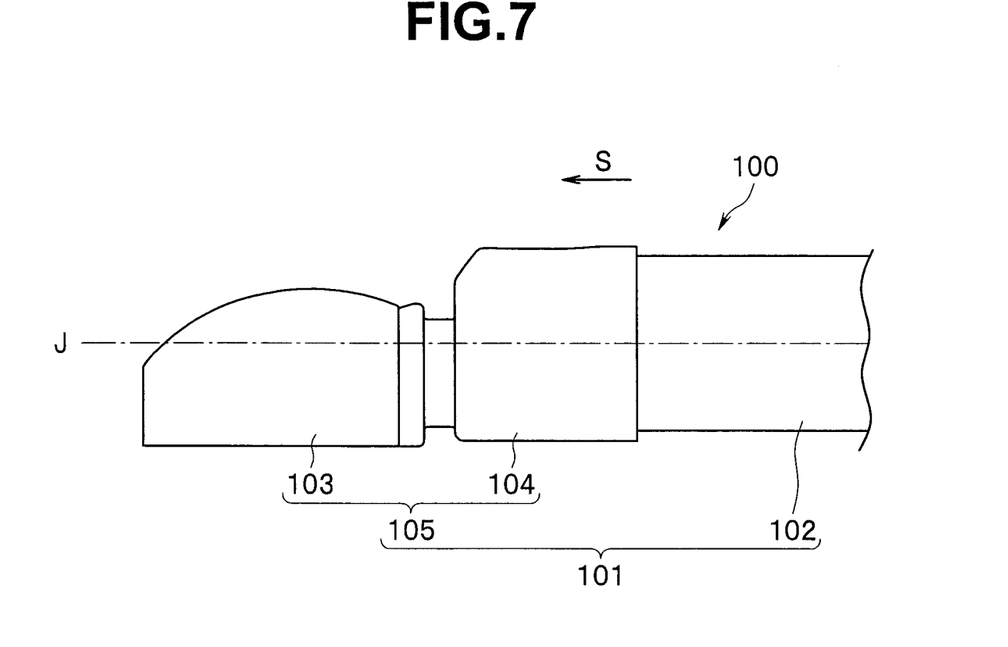
FIG. 7 is a diagram to show the distal end side of an insertion portion of a conventional ultrasound endoscope in which a distal end rigid portion along with a bending portion has a linear shape.
Figure 8:
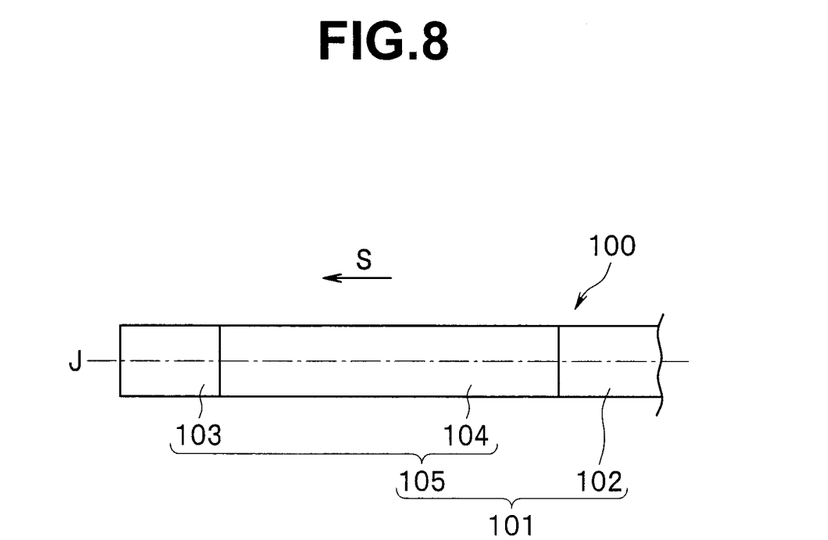
FIG. 8 is a diagram to schematically show the distal end side of the conventional insertion portion of FIG. 7.

FIG. 5 is a diagram to show the distal end side of an insertion portion of an ultrasound endoscope of the present embodiment, along with the distal end side of a conventional insertion portion shown in FIG. 7 in which a distal end rigid portion as well as a bending portion has a linear shape. FIG. 6 is a diagram to schematically show the distal end side of the insertion portion of the present embodiment of FIG. 5, along with the distal end side of a conventional insertion portion shown in FIG. 8, and the distal end side of an insertion portion in which a connection portion does not have a swept shape and an ultrasound observation section is bent.

As shown in FIG. 6, the ultrasound observation section 3 may also be inclined at an angle θ2 with respect to the direction of an axis J' which is parallel with the central axis J of the bending portion 2. As a result of this, the insertability of the insertion portion 1 will be further improved. It is noted that the reason why the insertability of the insertion portion 1 is improved by the arrangement that the ultrasound observation section 3 is bent at the angle θ2 will be described later as well.

Further, hereinafter, owing to the arrangement that the connection portion 4 is inclined from the central axis J at an inclination angle θ1 as shown in FIG. 5, although this is a common structure in the first to third embodiments, it becomes possible to bring a central axis H of a protrusion opening 4g provided in the area of a chain line D closer to being parallel with the central axis J. That is, it is possible to decrease the inclination angle of the central axis H with respect to the central axis J.

As a result of this, since a treatment instrument can be protruded from the protrusion opening 4g without being extremely bent along the central axis J, the insertability of the treatment instrument is improved. Further, it is also possible to suppress to a minimum the flexion of a known image guide or a light guide at the connection portion 4, which is inserted into the vicinity of the protrusion opening 4g in the insertion portion 1.

The ultrasound observation section 3 has a known convex type and includes an ultrasound transmission/reception section 3s, which transmits ultrasound C to an area to be inspected in the interior of the body and receives an echo single of the ultrasound C reflected from the area to be inspected, in a housing 3h which includes an acoustic lens 3n, as shown in FIG. 5. What is described so far is the common structure in the first to third embodiments.

Further, in the present embodiment, the acoustic lens 3n is positioned in the housing 3h such that the transmission direction of ultrasound C corresponds to the direction to the central axis J side.

Further, the ultrasound observation section 3 is positioned in a back face 3m side, which is an opposite direction side of a position at which the ultrasound C transmitted from the ultrasound transmission/reception section 3s intersects with the central axis J, that is, the opposite direction side of the transmission direction of ultrasound C, in the housing 3h with respect to the central axis J as shown in FIG. 5. In other words, a part of the ultrasound observation section 3 will not intersect with the central axis J. Moreover, the inclination angle θ1 of the connection portion 4 described above is set to be an angle at which a part of the ultrasound observation section 3 will not intersect with the central axis J.

Further, in the present embodiment, as described above, the ultrasound observation section 3 is positioned along a straight line W which intersects with a central axis Y, which is parallel with the central axis J, at an angle θ2 which is less than 90° and is also less than the inclination angle θ1 of the connection portion 4.

That is, the ultrasound observation section 3 is inclined with respect to the central axis J at an angle θ2 and having a swept shape. To be more specific, the inclination angle θ2 of the ultrasound observation section 3 corresponds to the inclination angle of the back face 3m of the housing 3h. Moreover, the inclination angle θ2 of the ultrasound observation section 3 is set to be an angle at which a part of the ultrasound observation section 3 will not intersect with the central axis J.

Thus, in the ultrasound endoscope 10 of the present embodiment, the connection portion 4 has a swept shape and the ultrasound observation section 3 has a swept shape as well. As a result of this, when supposing that the length of the ultrasound observation section be t1, and the length of the connection portion 4 be t2 as shown in FIG. 6, the length of the distal end rigid portion 5 in the direction S is shorter by an amount of m3 than the length of the distal end rigid portion 105 of the insertion portion 101 in the ultrasound endoscope 100, in which the distal end rigid portion 105 including a conventional ultrasound observation section 103 and a connection portion 104, and a bending portion 102 are provided in a linear fashion along the central axis J as shown in FIGS. 7 and 9.

Further, as shown in FIG. 6, the length of the distal end rigid portion 5 becomes shorter by an amount of m2 than that of the distal end rigid portion 505 in the ultrasound endoscope 500, in which the insertion portion 501 includes a distal end rigid portion 505 having a connection portion 504 which does not have a swept shape and an ultrasound observation section 503 which is bent without having a swept shape at an angle θ2, which is less than θ1 and less than 90°, from the distal end of the connection portion 504. It is noted that the connection portion 504 has a similar configuration to that of the connection portion 204 of the ultrasound endoscope 200.

Further, if a passing diameter r3 when the insertion portion 1 is made to proceed in a direction A while deforming a bronchus in the present embodiment is compared with a passing diameter R2 of an ultrasound endoscope 500 in which the connection portion 504 and the ultrasound observation section 503 do not have a swept shape, the result will be r3<r2.

That is, the passing diameter will be smaller in the case where not only the connection portion 4 but also the ultrasound observation section 3 has a swept shape and is being bent, as in the present embodiment.

It is noted that the arrangement that the ultrasound observation section 3 is only being bent at an angle θ2, which is less than θ1 and is less than 90°, without having a swept shape will contribute to shortening of the distal end rigid portion 5 and reduction of the passing diameter.

That is, the arrangement that the connection portion 4 only has a swept shape will contribute to shortening of the distal end rigid portion 5 and the reduction of the passing diameter. This is also true with the first and second embodiments described above.

Therefore, as shown in the first to third embodiments described above, the arrangement that the connection portion 4 has a swept shape will allow not only the length of the distal end rigid portion 5 to be shortened, but also the passing diameter r3 to be reduced, thus improving the insertability of the insertion portion 1.

Furthermore, the arrangement that the ultrasound observation section 3 is being bent to be parallel with the central axis J, or so as to have an angle θ2, or has a swept shape will further improve the insertability of the insertion portion 1.

This is because if the diameter of the insertion portion 1 to be inserted into, for example, a bronchus, that is, the passing diameter for the bronchus has become larger, or the length of the distal end rigid portion 5 in the direction S has become longer, when inserting the insertion portion 1 at a branching portion of superior and middle lobes selectively to either side of the branching portion, it is difficult to insert it into both sides or either one side, thus degrading the selectivity, and it is difficult to insert the insertion portion into a deeper part after inserting into either of superior lobe or middle lobe. Namely, that is because the insertability of the insertion portion is degraded.

Therefore, as the result of realizing reduction of the passing diameter of the insertion portion 1 and shortening of the distal end rigid portion 5 in the direction S, the insertability of the insertion portion 1 is improved.

Throughout the disclosure provided in this application, the term "swept shape" refers to a three-dimensional shape. As an example, FIG. 5 shows the swept shape of connection portion 4 as a three-dimensional shape defined by projecting the boundary of the interface Z along the straight line Q intersecting with the central axis J of the bending portion 2 while maintaining the perpendicularity of the interface Z with respect to the central axis J of the bending portion 2.

It is noted that although the ultrasound endo scope 10 has been shown taking an example of the configuration which is inserted into a bronchus, it can be, as a matter of course, applied to an ultrasound endo scope which is to be inserted into other sites.

What is claimed is:

1. An ultrasound endoscope comprising:
  a bending portion having a bending portion central axis, wherein the bending portion is configured to be controlled to bend between:
   a first arrangement in which the bending portion central axis is parallel with a predetermined direction; and
   a second arrangement in which the bending portion central axis is not parallel with the predetermined direction;
  an ultrasound observation housing comprising an acoustic lens through which an ultrasound signal is transmitted and an echo signal of the ultrasound signal is received; and a connection portion configured to connect the bending portion and the ultrasound observation housing, wherein an interface connects the bending portion and the connection portion, and wherein in the first arrangement:

the bending portion central axis is perpendicular to the interface;

a plane is perpendicular to the interface and includes the bending portion central axis;

the plane intersects with a periphery of the interface at a first interface point and a second interface point; and for each cross-section of the connection portion that is perpendicular to the bending portion central axis:

a periphery of the each cross-section of the connection portion intersects the plane at a first connection portion point and a second connection portion point; and a first line directly connecting the first connection portion point and the first interface point intersects the bending portion central axis, and a second line directly connecting the second connection portion point and the second interface point intersects the bending portion central axis.

2. The ultrasound endoscope according to claim 1, wherein the ultrasound observation housing is inclined with respect to the connection portion from a distal end of the connection portion.

3. The ultrasound endoscope according to claim 2, wherein the ultrasound observation housing is positioned in parallel with the bending portion central axis.

4. The ultrasound endoscope according to claim 2, wherein the ultrasound observation housing is inclined with respect to the bending portion central axis, and wherein a first inclination angle formed between the bending portion central axis and an a connection portion central axis of the connection portion is larger than a second inclination angle formed between the connection portion central axis and a ultrasound observation housing central axis of the ultrasound observation housing.

5. The ultrasound endoscope according to claim 4, wherein the ultrasound observation housing comprises a convex front face and a back face opposite to the convex front face, wherein the acoustic lens is arranged to the convex front face, and the ultrasound signal is transmitted through the acoustic lens in a direction intersecting the bending portion central axis, and wherein a third inclination angle formed between the back face of the ultrasound observation housing and the bending portion central axis is equal to the second inclination angle.

* * * * *